(12) United States Patent
Houston et al.

(10) Patent No.: US 11,033,377 B2
(45) Date of Patent: Jun. 15, 2021

(54) STENT

(71) Applicant: Vascular Flow Technologies Limited, Dundee (GB)

(72) Inventors: John Graeme Houston, Perth (GB); William David Allan, Cambridgeshire (GB); Craig Maxwell Dunlop, Glasgow (GB)

(73) Assignee: Vascular Flow Technologies Limited, Dundee (GB)

( * ) Notice: Subject to any disclaimer, the term of this patent is extended or adjusted under 35 U.S.C. 154(b) by 233 days.

(21) Appl. No.: 15/575,210

(22) PCT Filed: May 19, 2016

(86) PCT No.: PCT/GB2016/051449
§ 371 (c)(1),
(2) Date: Nov. 17, 2017

(87) PCT Pub. No.: WO2016/185219
PCT Pub. Date: Nov. 24, 2016

(65) Prior Publication Data
US 2018/0147046 A1     May 31, 2018

(30) Foreign Application Priority Data

May 19, 2015   (GB) .................................... 1508593

(51) Int. Cl.
*A61F 2/915* (2013.01)
*A61F 2/07* (2013.01)
*A61F 2/06* (2013.01)

(52) U.S. Cl.
CPC ................ *A61F 2/07* (2013.01); *A61F 2/915* (2013.01); *A61F 2002/068* (2013.01);
(Continued)

(58) Field of Classification Search
CPC ................................................ A61F 2002/068
See application file for complete search history.

(56) References Cited

U.S. PATENT DOCUMENTS

2002/0082675 A1* 6/2002 Myers ....................... A61F 2/07
                                                                    623/1.13
2002/0179166 A1* 12/2002 Houston ................... A61F 2/06
                                                                    138/39

(Continued)

FOREIGN PATENT DOCUMENTS

WO        0038591 A2      7/2000
WO       02098325 A2     12/2002
(Continued)

OTHER PUBLICATIONS

Officer B Fidalgo Marron, "International Search Report and the Written Opinion", PCT/GB2016/051449, dated Jul. 22, 2016, 12 pp.
(Continued)

*Primary Examiner* — Megan Y Wolf
(74) *Attorney, Agent, or Firm* — Kaplan Breyer Schwarz, LLP

(57) ABSTRACT

A stent (1) comprising a tubular frame (2) comprising a first end (3) and a second end and a longitudinal axis (4) therebetween. The frame (2) comprises a plurality of struts (9) defining a generally cylindrical portion comprising a longitudinally extending helical fin (11) protruding radially inwardly and having a helix angle. The angle, relative to the longitudinal axis (4), of at least some of the struts (9) in the helical fin (11) is substantially aligned with the helix angle of the helical fin (11).

13 Claims, 12 Drawing Sheets

(52) U.S. Cl.
CPC ............... *A61F 2002/91558* (2013.01); *A61F 2230/0091* (2013.01); *A61F 2240/00* (2013.01)

(56) References Cited

U.S. PATENT DOCUMENTS

| | | | | |
|---|---|---|---|---|
| 2006/0265051 A1* | 11/2006 | Caro | ......................... | A61F 2/07 623/1.17 |
| 2007/0106373 A1* | 5/2007 | Houston | ................. | F15D 1/065 623/1.32 |
| 2007/0250148 A1* | 10/2007 | Perry, Jr. | .................. | A61F 2/91 623/1.11 |

FOREIGN PATENT DOCUMENTS

| | | |
|---|---|---|
| WO | 03103540 A1 | 12/2003 |
| WO | 2004047908 A2 | 6/2004 |
| WO | 2004082533 A1 | 9/2004 |
| WO | 2005004751 A1 | 1/2005 |
| WO | 2005092240 A1 | 10/2005 |
| WO | 2010133821 A1 | 11/2010 |
| WO | 2014134352 A1 | 9/2014 |

OTHER PUBLICATIONS

Duda et al., Physical Properties of Endovascular Stents: An Experimental Comparison, SCVIR, JVIR, May 2000, vol. 11, pp. 645-654.

\* cited by examiner

STENT

FIELD OF THE INVENTION

The present invention relates to a stent. In particular, the present invention relates to a stent having a helical fin for effecting fluid flow patterns and having resistance against radial force and fatigue and methods for producing same.

BACKGROUND

A stent is a type of vascular prosthesis suitable for implantation within a vessel of a patient. There are many different types of stents used for a wide variety of different purposes. Common types of stent include coronary stents, peripheral arterial and venous stents and biliary stents. Coronary, peripheral arterial and venous stents are often used to treat stenotic, i.e. narrowed arteries or veins caused by the thickening of the arterial or venous walls due to the formation of plaques along the inner surface, or to help to provide structure to weakened and damaged blood vessels that are susceptible to tearing. Biliary stents are used to relieve narrowing of the bile duct (bile stricture), which can be caused by cancer of the bile duct or by injury during surgery.

Coronary artery stents and peripheral arterial and venous stents are implanted using a procedure called angioplasty. During this procedure, the stent is inserted into a vessel of a patient in a crimped configuration of a first diameter. This crimped shape makes it possible to manoeuvre the stent into the correct position within the vessel. Once in place, the stent is then expanded to a second diameter against the inner wall of the vessel, thus opening the vessel lumen and allowing the stent to be retained within the vessel. The stent may be self-expanding or manually expandable using a balloon catheter. In order to maintain an expanded configuration within the blood vessel, a stent must have sufficient radial strength to resist compression to prevent it from collapsing or becoming misshapen due to the inward force of the blood vessel. A typical stent has a radial resistive force of 0.39 to 1.65 N/cm (Duda et al, JVIR 2000; 11:645-654).

One of the most widely used materials in the manufacture of stent frames is nickel-titanium also known as nitinol. Nitinol is a shape memory alloy that undergoes a phase transformation from a weaker more deformable martensite phase exposed to low temperatures to a stronger austenite phase when exposed to certain higher temperatures. Thus, when exposed to a low temperature e.g. below room temperature, the stent frame can be easily deformed into a desired shape, e.g. a crimped configuration and once heated to its transformation temperature, e.g. when exposed to body temperature, it expands to its "memory shape". This resilient nature makes nitinol an ideal candidate material for self-expanding stents.

WO00/38591 discloses the concept of a spiral formation on the internal surface of stents to induce desirable helical flow in blood flowing through the lumen of the stent. Generating a helical or spiral flow pattern in the blood serves to reduce turbulence and dead spots which can lead to plaque formation, thus reducing vascular disease.

WO02/098325 discloses an apparatus for forming a helical flow formation in a conduit wherein the apparatus comprises a helical structure. The apparatus is adapted to be located around the exterior of, and engaged with, a conduit carrying a fluid, in use, such that the helical structure forms the helical flow formation inside the conduit by imposing, maintaining and/or reinforcing the shape of the helical flow formation. It is to be understood that, since the helical structure is located around the exterior of the conduit, it plays no role in maintaining the patency of the conduit.

However, one of the problems with introducing a helical structure into a stent or other structure, particularly into a frame having a mesh geometry, is that the helical structure can cause parts of the stent/structure frame to become weakened. This weakening increases the risk of stent/structure fractures forming in the frame when under stress due to biomechanical forces or when being implanted during surgery. Stent/structure fractures can be complete or partial and can occur in isolated struts or comprise a complete transverse stent/structure fracture with complete displacement of stent/structure segments. Therefore, there is a need to provide a stent having a helical formation which avoids the occurrence of fractures but without compromising on characteristics such as flexibility, radial force and fatigue resistance.

The current invention serves to alleviate one or more of the above problems.

SUMMARY OF THE INVENTION

In accordance with a first aspect of the invention there is provided a stent comprising a tubular frame comprising a first end and a second end and a longitudinal axis therebetween, wherein the frame comprises a plurality of struts defining a generally cylindrical portion comprising a longitudinally extending helical fin protruding radially inwardly and having a helix angle and wherein the angle, relative to the longitudinal axis, of at least some of the struts in the helical fin is substantially aligned with the helix angle of the helical fin.

Preferably, the angle of the struts relative to the longitudinal axis is substantially the same as the helix angle.

Preferably, at least some of the struts in the tubular frame are arranged in a series of repeating elements and, in the repeating elements located in the helical fin, at least 10% of the total strut length in each repeating element is substantially aligned with the helical fin, preferably at least 20%, 30%, 40% or 50% of the total strut length.

Preferably, the struts delineate a plurality of circumferential rings having a waveform.

Still preferred, each circumferential ring is located adjacent to each other parallel to the longitudinal axis to define the tubular shape of the stent frame.

Typically, the waveform comprises an amplitude extending parallel to the longitudinal axis. Preferably, the waveform comprises a plurality of peaks and troughs. Still preferred, the plurality of peaks extends towards the first end of the frame and the plurality of troughs towards the second end of the frame.

Typically, the waveform is a triangle waveform, or a sine waveform or a complex waveform, or a square waveform.

Preferably, each trough is connected to a peak by a connecting strut and the angle of each trough-to-peak connecting strut within the helical fin is substantially aligned with the helical angle of the helical fin.

Preferably, the angle of each trough-to-peak connecting strut extending to the peak towards the centre of the helical fin and which is in the helical fin is substantially aligned with the helix angle of the helical fin. Preferably, the angle of each trough-to-peak connecting strut extending to the peak away from the centre of the helical fin and which is in the helical fin is the mirror angle of the helix angle of the helical fin.

Alternatively, the angle of the other-most trough-to-peak connecting struts within the helical fin is substantially aligned with the helical axis of the helical fin.

Preferably, the angle of the trough-to-peak connecting struts is substantially the same as the helical angle.

Preferably, the angle of the trough-to-peak connecting struts is the mirror angle of the helical angle.

Preferably, the angle is within 1° of the helical angle. Preferably, the angle is within 2° to 10°, preferably within 5°.

Preferably, each successive trough in adjacent rings extends parallel.

It is preferred that the helical fin may have a helix angle of between 5° and 50° with the longitudinal axis of the stent frame. For example, the helical fin may have a helix angle of between 5° and 25°, preferably between 18° to 22°; or it may be between 20° to 40°.

Preferably, the helix angle will be such that the helical fin completes at least one whole turn around the longitudinal axis of the stent frame within the length of the stent.

The helical fin may be any cross-sectional shape.

The cross-sectional shape of the helical fin may be symmetric or asymmetric.

Preferably, the stent elements are of a waveform with non-consistent pattern.

In accordance with a preferred embodiment of the invention there is provided a stent having a tubular frame comprising a first (distal) end and a second (proximal end) end and a longitudinal axis therebetween, wherein the frame is defined by a number of stent elements, said stent elements comprising circumferential rings having a waveform comprising a plurality of peaks and troughs extending parallel to the longitudinal axis, wherein the plurality of peaks extend towards the first end of the frame and the plurality of troughs extend towards the second end of the frame, wherein each trough is connected to a peak by a connecting strut, wherein the frame further comprises a helical fin protruding inwardly and having a helix angle and wherein the angle of each trough-to-peak connecting strut relative to the longitudinal axis within the helical fin is aligned with the helix axis of the helical fin.

Preferably, wherein the angle of each trough-to-peak connecting strut extending to the peak towards the centre of the helical fin and within the helical fin is substantially the same as the helix angle.

Preferably, the rings may comprise a number of cells. The cells may be of any shape, for example a diamond shape. The cells may be of any size. The cells may be open cells or closed cells. The ring may comprise a combination of open cells and closed cells.

Advantageously, the frame is crimpable or deformable such that is permits expansion of the stent.

Preferably, the frame is composed of a self-expanding material. Preferably, the self-expanding material is nickel titanium (nitinol).

Alternatively, the frame comprises stainless steel or cobalt-chromium alloy.

Preferably, the frame is a bare-metal frame, preferably comprising stainless steel.

Typically, the stent further comprises at least one cover. Preferably, the cover is radially expandable. Advantageously, the cover comprises polytetrafluoroethylene (PTFE).

In a preferred embodiment, the helical fin is formed by the deformation of at least a portion of a side wall of the frame. Preferably, the helical fin extends along the entire length of the frame. Alternatively, the helical fin extends along a portion of the length of the frame.

In a preferred embodiment, the frame further comprises at least one cover or sleeve. Preferably, the cover or sleeve is radially expandable. Advantageously, the cover or sleeve comprises polytetrafluoroethylene (PTFE). Typically, the cover or sleeve surrounds the entire frame. Alternatively, the cover or sleeve is over a portion of the frame. The cover or sleeve may be located over a portion or the entire inner surface and/or over a portion or the entire outer surface. Preferably, the cover is over the inner and/or outer surface of the helical fin only.

Alternatively, the cover or sleeve is located over the inner surface of the frame only. Alternatively, the cover or sleeve is positioned over the outer surface of the frame only.

Typically, the cover is heat sealed to the frame.

In a preferred embodiment, the stent comprises a cover or sleeve located over the inner surface and a cover or sleeve positioned over the outer surface of the frame wherein the inner and outer covers are attached together at a position between the openings of wall of the frame.

The frame may be of any geometry. The frame may be braided. The frame may be wire-wound or a wire mesh.

Typically, the cover is non-removable from the frame. Alternatively, the cover is at least partially or fully removable from the frame.

Still preferred, the stent of the present invention has a crimped configuration of a first diameter to allow insertion into a vessel of a patient and an expanded configuration of a second diameter. At the second diameter, the outer surface of the frame contacts the inner surface of the vessel.

Preferably, the frame may comprise parts having at least two different diameters. Alternatively, the frame may have a consistent diameter along its entire length.

The frame may be coated.

In a second aspect of the current invention, there is provided a stent blank comprising a tubular frame comprising a first end and a second end and a longitudinal axis therebetween, wherein the frame comprises a plurality of struts defining a generally cylindrical portion comprising a longitudinally extending helical element having a helix angle and capable of being deformed to form a longitudinally extending helical fin protruding radially inwardly and wherein the angle of at least some of the struts, relative to the longitudinal axis, is substantially aligned with the helix angle.

Preferably, at least some of the struts in the tubular frame are arranged in a series of repeating elements and, in the repeating elements located in the helical element, at least 10% of the total strut length in each repeating element is substantially in line with the helical fin, preferably at least 20%, 30%, 40% or 50% of the total strut length.

Preferably, the struts delineate a plurality of circumferential rings having a waveform.

Still preferred, each circumferential ring is located adjacent to each other parallel to the longitudinal axis to define the tubular shape of the stent frame.

Typically, the waveform comprises an amplitude extending parallel to the longitudinal axis. Preferably, the waveform comprises a plurality of peaks and troughs. Still preferred, the plurality of peaks extends towards the first end of the frame and the plurality of troughs towards the second end of the frame.

Typically, the waveform is a triangle waveform, or a sine waveform or a complex waveform, or a square waveform.

Preferably, each trough is connected to a peak by a connecting strut and the angle of each trough-to-peak connecting strut within the helical line is substantially aligned with the helical angle of the helical fin.

Preferably, the angle of each trough-to-peak connecting strut extending to the peak towards the centre of the helical element and which is in the helical element is substantially aligned with the helix angle of the helical element. Preferably, the angle of each trough-to-peak connecting strut extending to the peak away from the centre of the helical element and which is in the helical element is the mirror angle of the helix angle of the helical element.

Alternatively, the angle of the outermost trough-to-peak connecting struts within the helical element is substantially aligned with the helical axis of the helical line.

Preferably, the angle of the trough-to-peak connecting struts is substantially the same as the helical angle.

Preferably, the angle of the trough-to-peak connecting struts is the mirror angle of the helical angle.

Preferably, the angle is within 1° of the helical angle. Preferably, the angle is within 2° to 10°, preferably within 5°.

Preferably, each successive trough in adjacent rings within the helical element is aligned.

It is preferred that the helical element may have a helix angle of between 5° and 50° with the longitudinal axis of the stent frame. For example, the helical element may have a helix angle of between 5° and 25°, preferably between 18° to 22°; or it may be between 20° to 40°.

Preferably, the helix angle will be such that the helical fin completes at least one whole turn around the longitudinal axis of the stent frame within the length of the stent.

Advantageously, the frame is crimpable or deformable such that is permits expansion of the stent.

Preferably, the frame is composed of a self-expanding material. Preferably, the self-expanding material is nickel titanium (nitinol).

Alternatively, the frame comprises stainless steel or cobalt-chromium alloy.

Preferably, the frame is a bare-metal frame, preferably comprising stainless steel.

In a preferred embodiment, the stent blank of the invention is used in the method of the invention.

In a third aspect of the current invention, there is provided a method for forming the stent having a helical fin. The method comprises supporting a starting material on a mandrel having female helical groove and placing a helical former having a corresponding male helical ridge around the material so as to deform the material to have an internal helical fin corresponding to the shape of the groove upon compression of the helical former onto the mandrel. The method further comprises setting the material in that configuration, and removing the helical former and the mandrel to form the stent. Preferably, the method comprises a step of providing a frame wherein the angle of the struts within the portion of the frame which forms the helical fin is substantially aligned with the helical angle of the helical fin. Alternatively, the method comprises a step of producing a frame wherein the angle of the struts within the portion of the frame which forms the helical fin is substantially aligned with the helical angle of the helical fin.

Preferably, the method comprises a step of producing a frame of the stent of the current invention as outlined in the previous aspect.

According to a fourth aspect of the present invention, there is provided a method of producing a stent having a helical fin comprising
(a) producing or providing a stent blank according to the invention;
(b) placing the stent blank on a mandrel having a female helical groove;
(c) clamping the stent blank on the mandrel with a helical former having a corresponding male helical ridge;
(d) heat treating the stent blank at a temperature suitable to deform the material from which the stent blank is made until the material has been uniformly exposed to said temperature in order to form the stent; and
(e) removing the stent from the mandrel.

Alternatively, the method comprises:
(a) Producing or providing a frame of a first diameter wherein the angle of the struts within the portion of the frame which forms the helical fin is substantially aligned with the helical angle of the helical fin.
(b) Placing the frame on a mandrel of a second diameter
(c) Heat treating the frame at a temperature suitable to deform the material for a time until the material has been uniformly exposed to the temperature
(d) Placing the frame on a mandrel of a third diameter, preferably having a female helical groove
(e) Clamping the frame on the mandrel with a helical former having a corresponding male helical ridge
(f) Heat treating the frame at a temperature suitable to deform the material until material has been uniformly exposed to said temperature and
(g) Removing the frame from the mandrel.

The method further comprises repeating step (d) to (f) on a mandrel of a fourth diameter prior to step (g).

Alternatively, the method comprises:
(a) Producing or providing a frame of a first diameter wherein the angle of the struts within the portion of the frame which forms the helical fin is substantially aligned with the helical angle of the helical fin.
(b) Placing the frame on a mandrel of a second diameter
(c) Heat treating the frame at a temperature suitable to deform the material for a time until the material has been uniformly exposed to the temperature
(d) Placing the frame on a mandrel of a third diameter
(e) Heat treating the frame at a temperature suitable to deform the material for a time until the material has been uniformly exposed to the temperature
(f) Placing the frame on a mandrel of a fourth diameter preferably having a female helical groove
(g) Clamping the frame on the mandrel with a helical former having a corresponding male helical ridge
(h) Heat treating the frame at a temperature suitable to deform the material until material has been uniformly exposed to said temperature and
(i) Removing the frame from the mandrel.

Preferably, the frame is produced by laser cutting the starting material into a desired geometry. The frame may be spun, moulded or extruded into the required shape or geometry.

Preferably, wherein the material is nitinol, the method comprises
(a) Producing or providing a nitinol frame of a first diameter wherein the angle of the struts within the portion of the frame which forms the helical fin is substantially aligned with the helical angle of the helical fin.
(b) Placing the frame on a mandrel of a second diameter
(c) Heat treating the nitinol frame at a temperature of between 400° C. and 600° C. for a time between about 5 minutes and 60 minutes.
(d) Placing the heat treated nitinol frame on a mandrel of a third diameter (e) Heat treating the nitinol frame at a temperature of between 400° C. and 600° C. for a time between about 5 minutes and 60 minutes.

(f) Placing a nitinol frame on a mandrel of a fourth diameter having a helical groove (g) Clamping the nitinol frame on the mandrel with a helical former having a corresponding male helical ridge (h) Heat treating the nitinol frame at a temperature of between 400° C. and 600° C. until material has been uniformly exposed to the temperature, preferably for between about 5 to 60 minutes, and (i) Removing the nitinol frame from the mandrel.

Preferably, the diameter of the mandrel increases at each placement step.

Preferably, the first diameter may be between 2 mm and 4 mm. The second diameter may be between 4 and 8 mm. The third diameter may be between 6 and 12 mm. The fourth diameter may be between 8 mm and 16 mm.

Preferably, the first diameter is a quarter of the final diameter.

Typically, the method further comprises electropolishing the frame.

Preferably, the method further comprises applying a cover to the frame.

Advantageously, a pharmaceutically active agent is releasably associated with the stent.

In this specification, the term "stent" refers to a mechanical structure which, when inserted in a vessel such as a blood vessel, exerts outwardly-directed radial force sufficient to maintain vessel patency in a range of anatomical sites undergoing physiological external compression/torsion and shortening. In some embodiments, a stent has a radial resistive force of at least 0.1 N/cm, preferably at least 0.39 N/cm, such as 0.39 to 1.65 N/cm (as measured by the test of nitinol stents in Duda et al ibid).

The terms "helical", "helix" and "spiral" as used herein cover the mathematical definition of helical and any combination of the mathematical definitions of helical and spiral.

A "helix angle" referred to herein is the angle between the helix and the axial line about which it is formed, in particular the longitudinal axis of a tubular frame.

The term "generally cylindrical" means a product whose shape approximates to that of a cylinder in the sense that a cross-section of the product perpendicular to the longitudinal axis thereof is approximately circular. It includes, for example, a product whose cross-section is a polygon of more than 10 sides but is not precisely circular.

The term "wave form" means a component, in particular a circumferential ring, whose shape oscillates along its length. The oscillation is in a direction defined as the amplitude of the wave. The oscillation may be a smooth curve such as a sine wave or may be angular such as a triangle wave form.

The term "diamond-shaped" refers to a connecting cell that is comprised of two pairs of parallel struts that intersect each other and have substantially the same length as each other.

The term "cell" refers to a segment of the stent frame comprising a number of struts. The cell can be open or closed. A "closed cell" is a segment that is connected at each junction of the segment. An "open cell" is one at least at least one junction of the segment is not connected. The cell can be of any shape or size.

The term "substantially aligned" is taken to mean for the most part equal and within 1° to 10°, preferably 5°.

DETAILED DESCRIPTION OF THE INVENTION

Embodiments of the stent structures encompassed by the current invention are described below, although the invention is not intended to be limited by these examples.

The current invention provides a stent having a tubular frame comprising a first (distal) and a second (proximal) end and a longitudinal axis therebetween. The frame comprises a plurality of struts defining a cylindrical portion comprising a longitudinally extending helical fin protruding radially inwardly and having a helix angle. The angle of some of the struts in the helical fin (relative to the longitudinal axis of the tubular frame) is substantially aligned with the helix angle of the helical fin. Aligning the angle of the struts with that of the helical fin imparts resistance against radial force and fatigue when within a patient vessel, thereby preventing the formation of fractures within the stent frame. The stent of the invention provides sufficient strength to resist compression, whilst maintaining desirable flexibility and the helical fin imparts spiral flow on fluid (e.g. blood) passing through the stent.

The helix angle to achieve such flow depends on factors such as diameter of the stent, longitudinal and rotational velocity of the fluid and the viscosity of the fluid. Typically, the helical fin effects a rotational flow of fluid within the tubular stent when in use. The rotational flow may comprise a helical or spiral flow.

Figure 1:
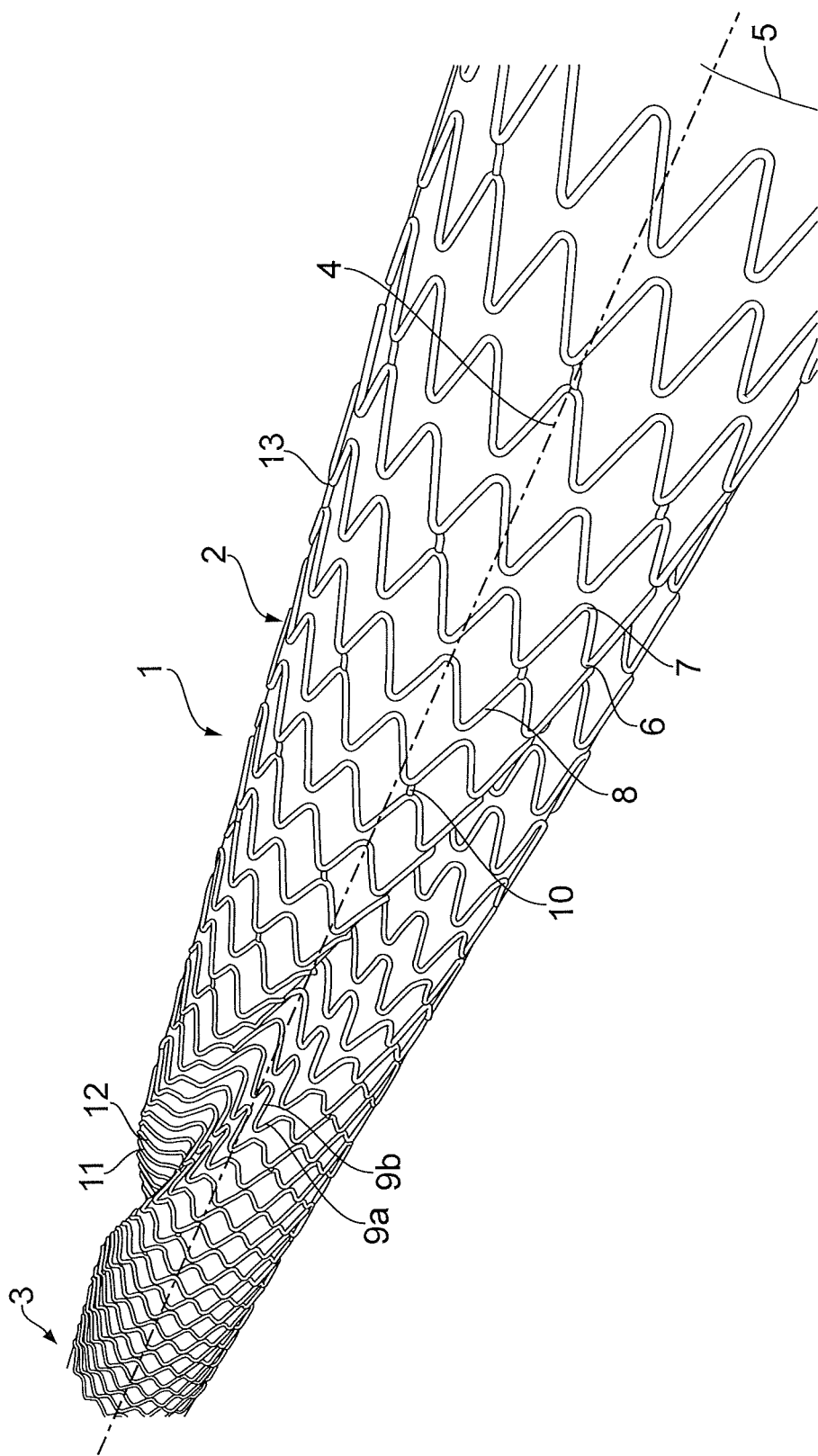
FIG. 1 is a perspective view of a stent of the invention having a helical fin and fitted on a mandrel.

FIG. 1 depicts a stent 1 of one embodiment of the present invention. The stent has a tubular frame 2 having a first end (distal) 3 and a second end (proximal; not shown) and a longitudinal axis 4 therebetween. The stent frame is depicted fitted on a mandrel 5 used to support the frame during the manufacturing of the stent but it is to be understood that the mandrel 5 is not present when the stent 1 is in use. The tubular frame 2 comprises a network of struts in the form of a series of undulating rings 13 disposed circumferentially along the longitudinal axis 4 of the frame. The rings are parallel to each other. The rings 13 are in a rounded triangle wave form having a plurality of peaks 6 extending towards the first end 3 and a plurality of troughs 7 extending towards the second end. Each peak 6 and trough 7 forms a V-shaped bend 8 in the same plane as the cylindrical surface defined by the tubular frame. The trough 7 of each V-shaped bend is connected to its respective peak 6 via a trough-to-peak connecting strut 9. Each ring is connected to its adjacent ring by a plurality of linker-struts 10 which extend between adjacent rings 13. Each linker-strut connects the trough of one V-shaped bend of a first ring to the peak of the adjacent V-shaped bend of an adjacent ring. Every fourth trough in each ring is connected to an adjacent peak on an adjacent ring.

A portion of the side wall of the frame 2 is deformed radially inwardly to form a longitudinally extending helical fin 11. The helical fin defines an inducer path 12. As is shown in more detail in FIG. 2, the angle, relative to the longitudinal axis, of each trough-to-peak connecting strut 9a of each V-shaped bend 8 that extends towards the centre of the helical fin (i.e. that is present in the portion of one side wall that forms the helical fin) is substantially the same as the helix angle 14 of the inducer path 12. The angle, relative to the longitudinal axis, of each peak-to-trough connecting struts 9 of each V-shaped bend 8 that extends away from the centre of the helical fin (i.e. that are present in the portion of the other side wall that forms the helical fin) is the mirror angle of the helix angle (i.e. the helix angle 14 minus the angle 15 between the trough-to-peak connecting strut 9a and its adjacent peak-to-trough connecting strut 9b).

The trough 7 of each V-shaped bend 8 that is within the helical fin 11 is aligned along the helical fin 11. This provides a substantially uniform geometry within the portion of the frame 2 forming the helical fin 11.

Figure 2:
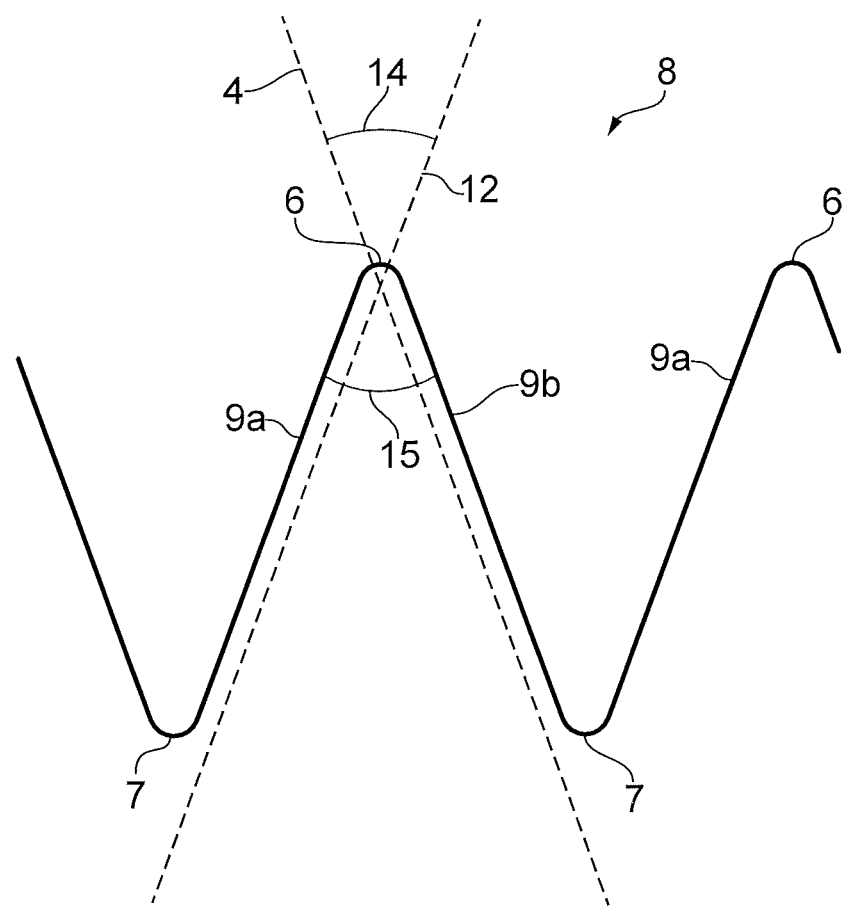
FIG. 2 is a view of a V-shaped bend from within the helical fin of the frame of FIG. 1.
Figure 3:
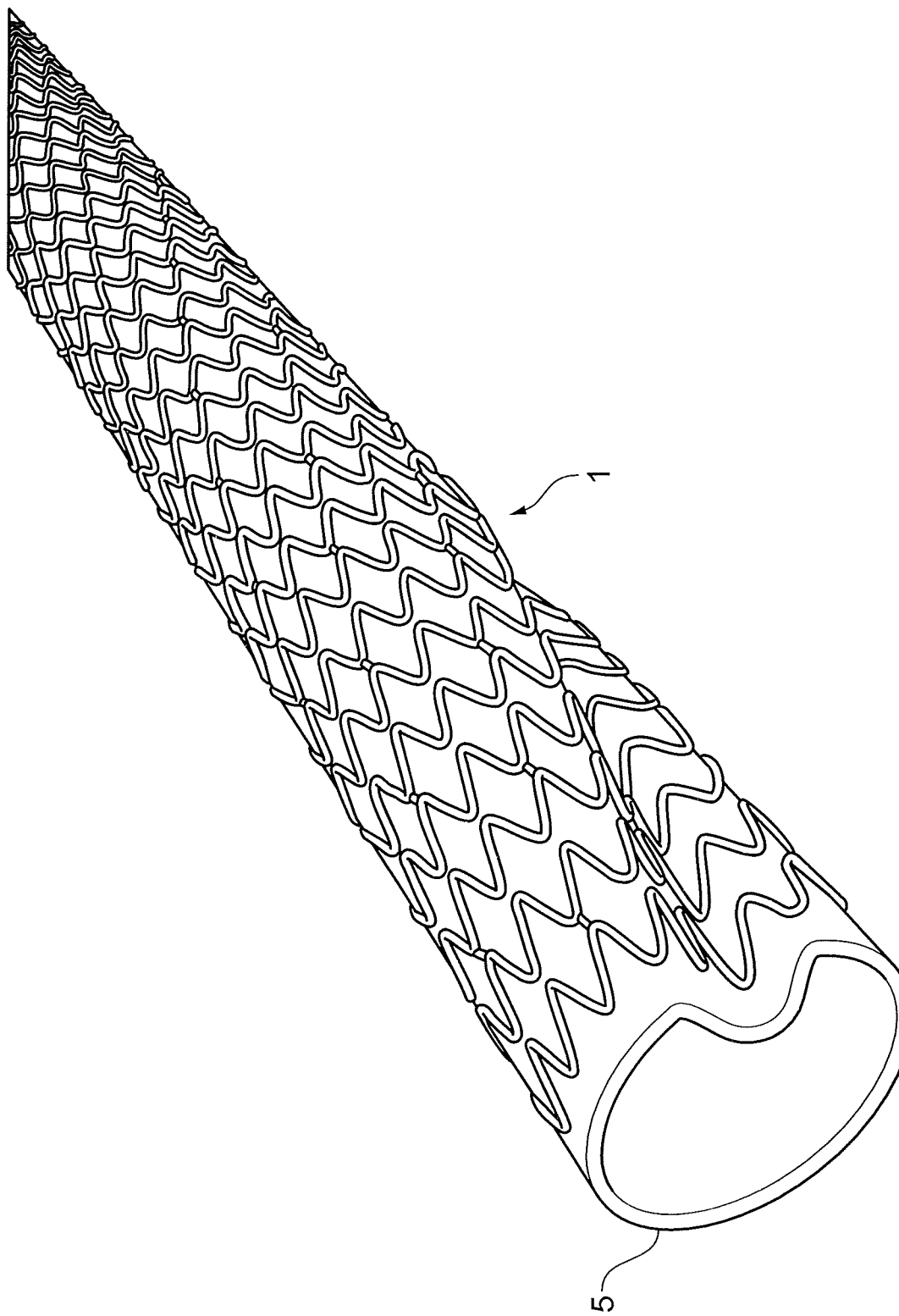
FIG. 3 is a perspective view of the stent of FIG. 1.
Figure 4:
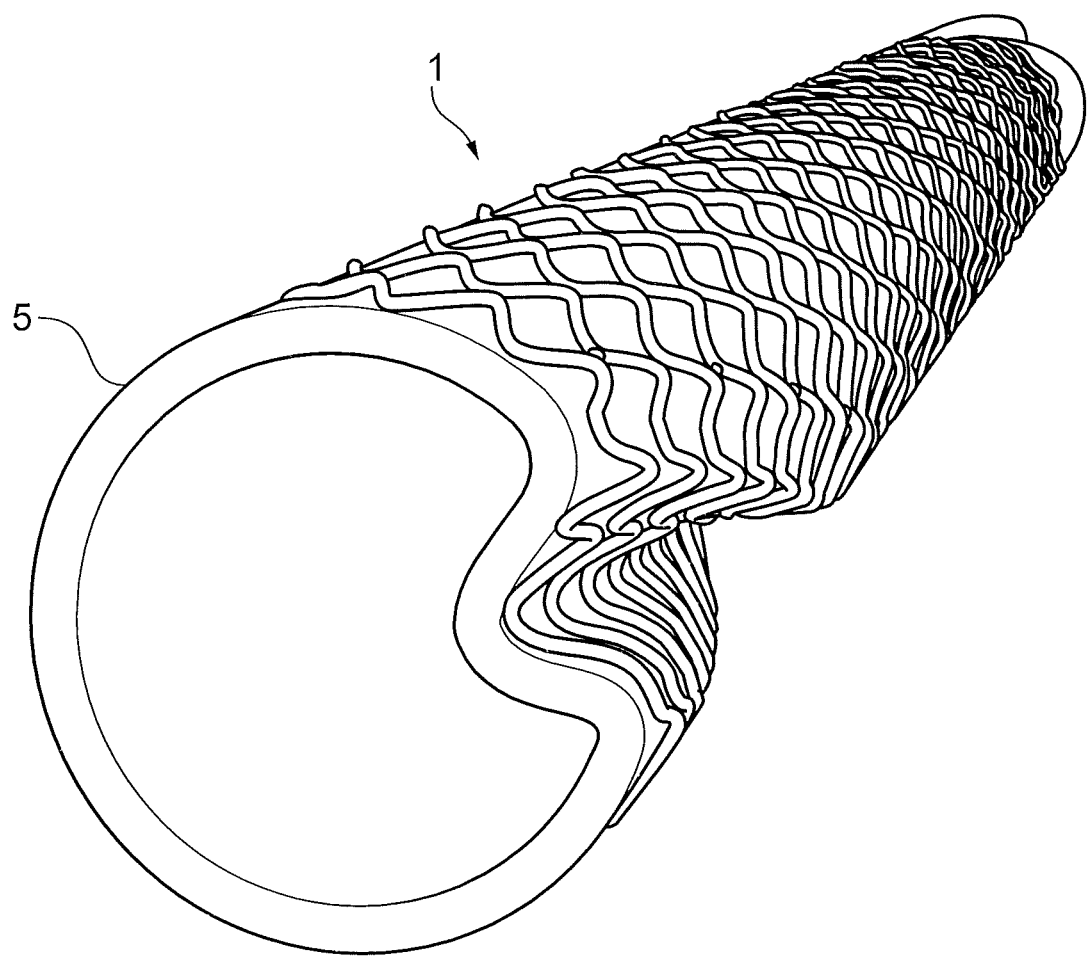
FIG. 4 is a perspective view of the stent of FIG. 1.
Figure 5:
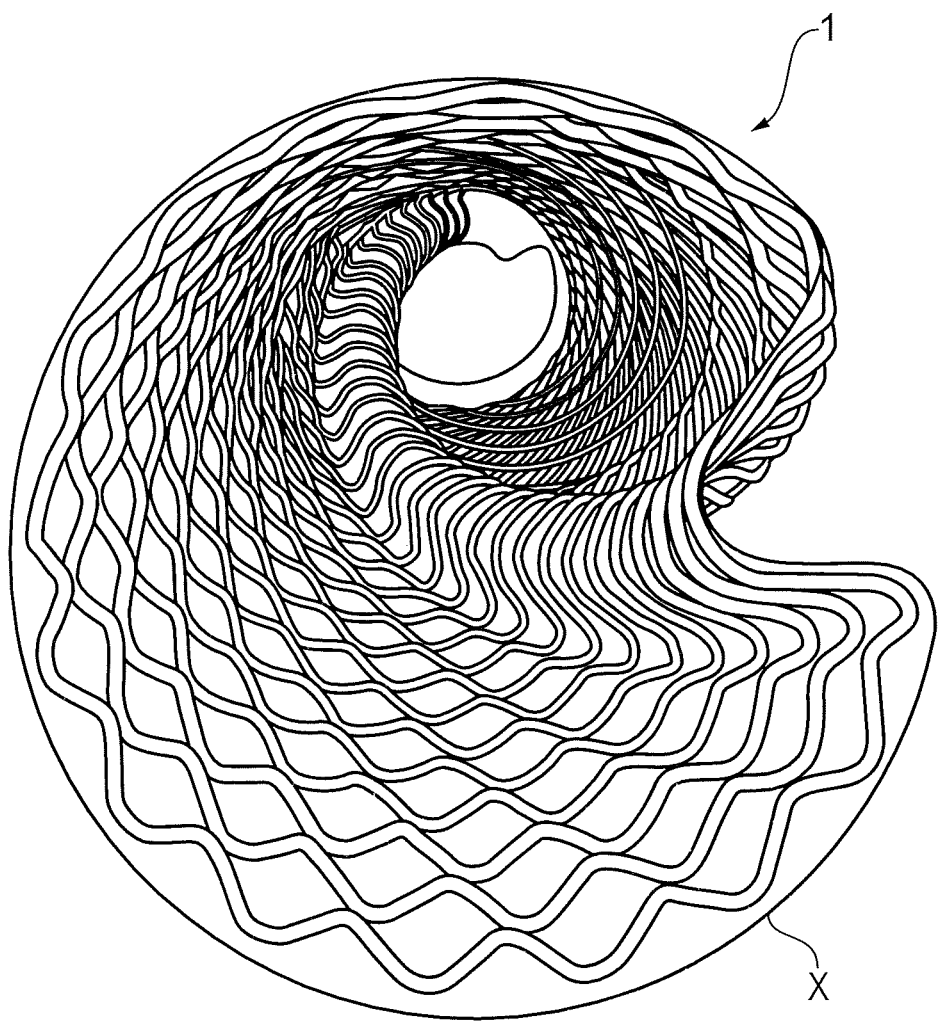
FIG. 5 is a view of the interior of the stent of FIG. 1 from the first end.
Figure 6:
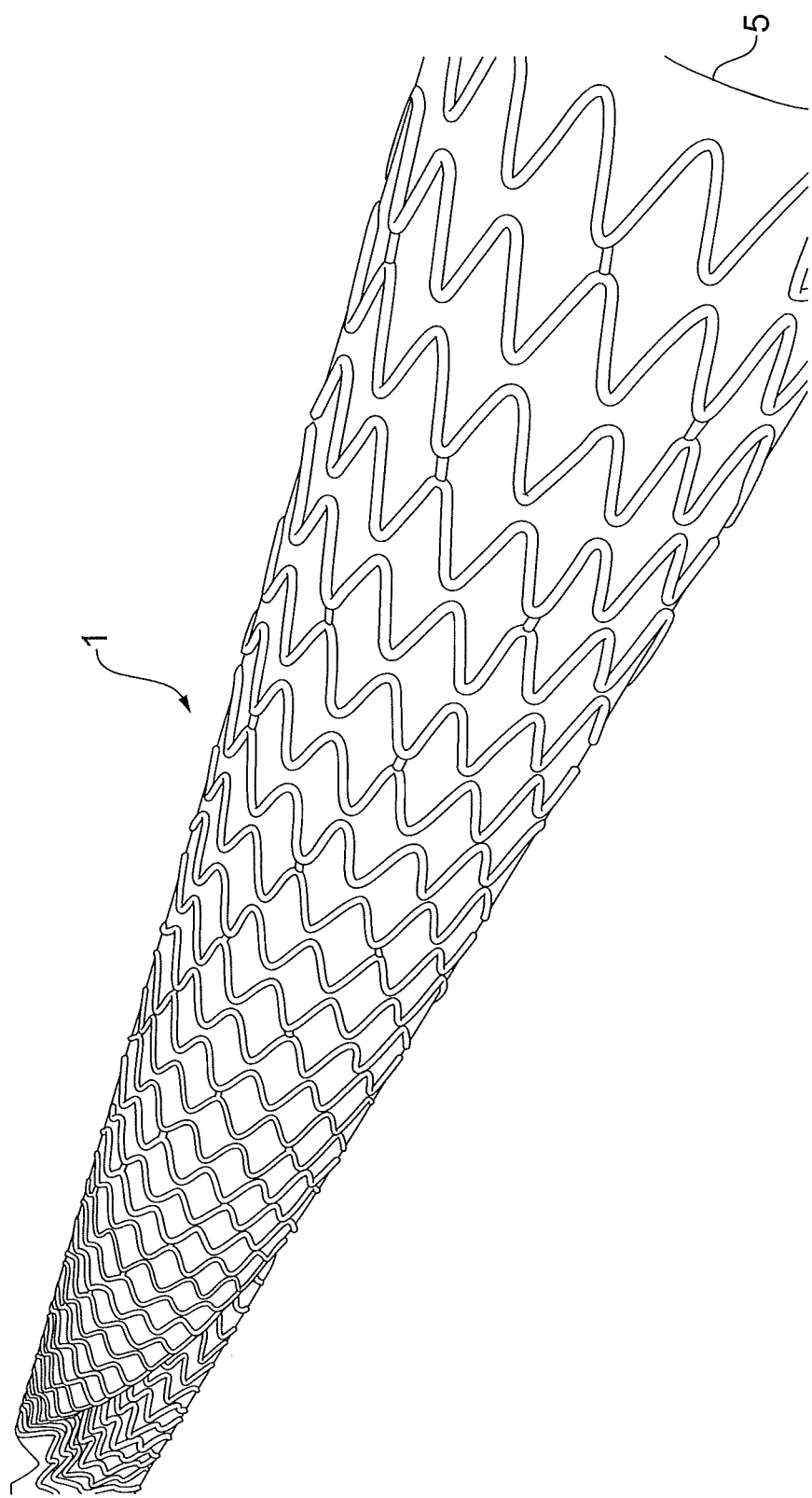
FIG. 6 is a perspective view of the stent of FIG. 1.
Figure 7:
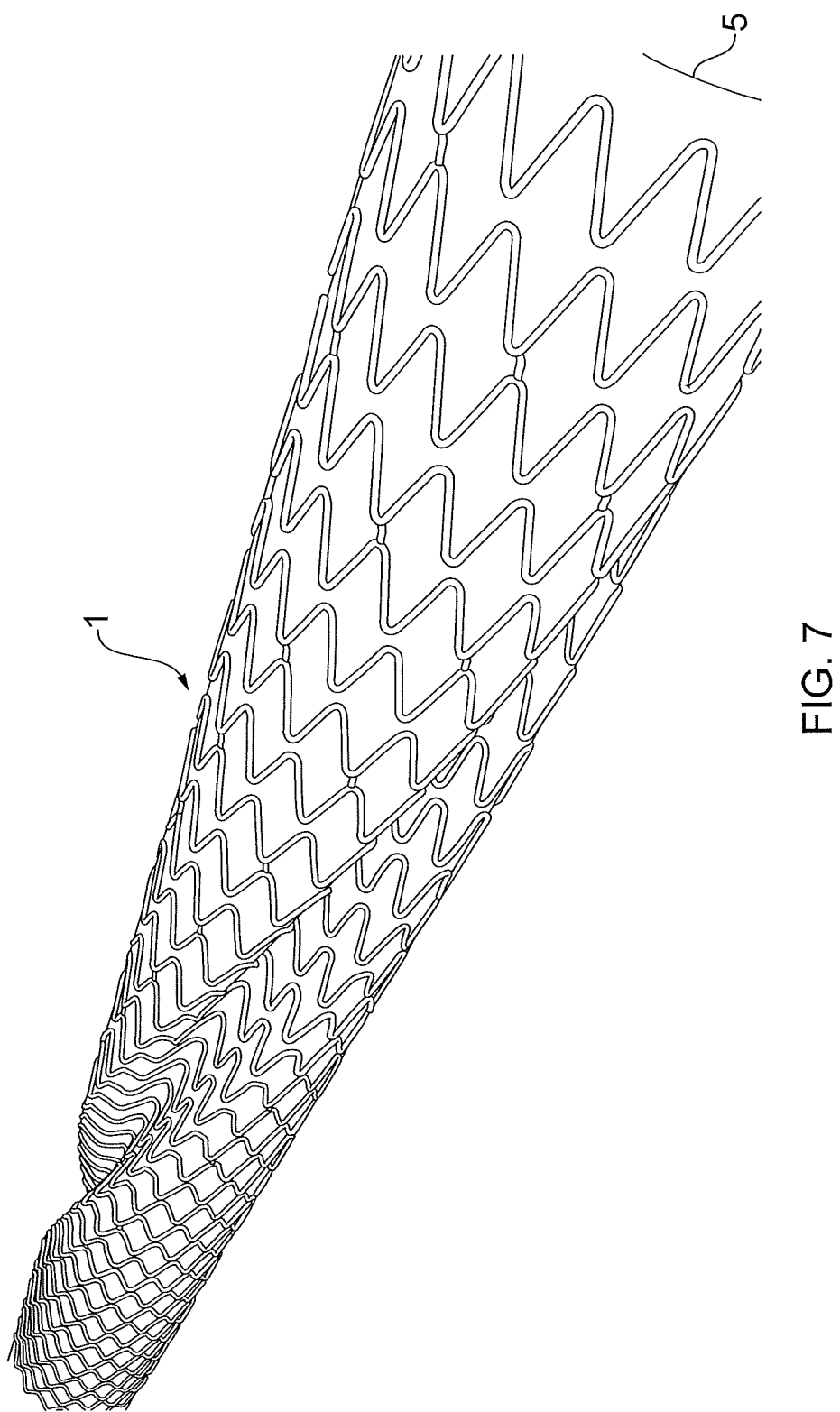
FIG. 7 is a perspective view of the stent of FIG. 1.
Figure 8:
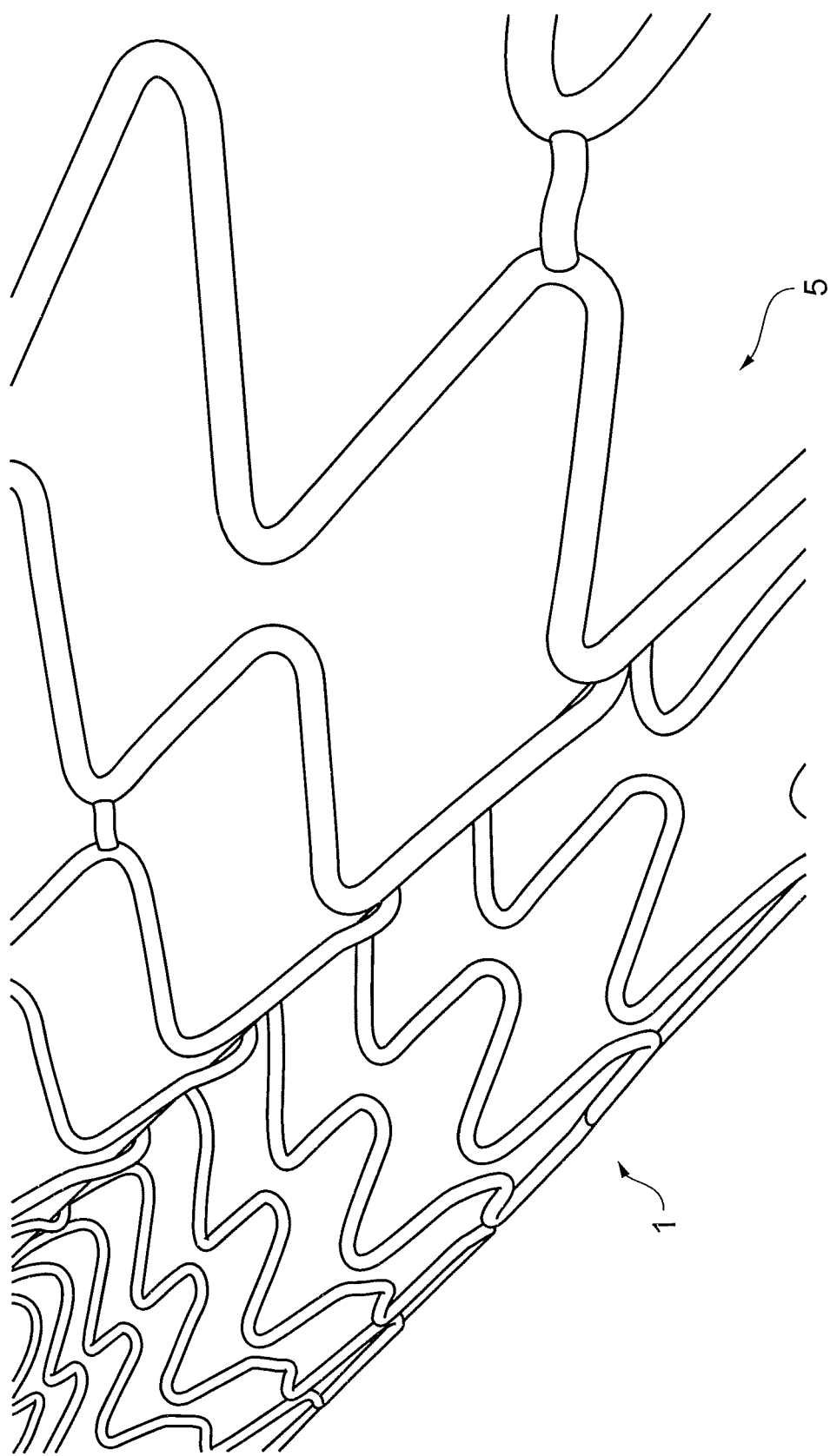
FIG. 8 is a perspective view of a portion of the stent of FIG. 1, including a portion of the helical fin.
Figure 9:
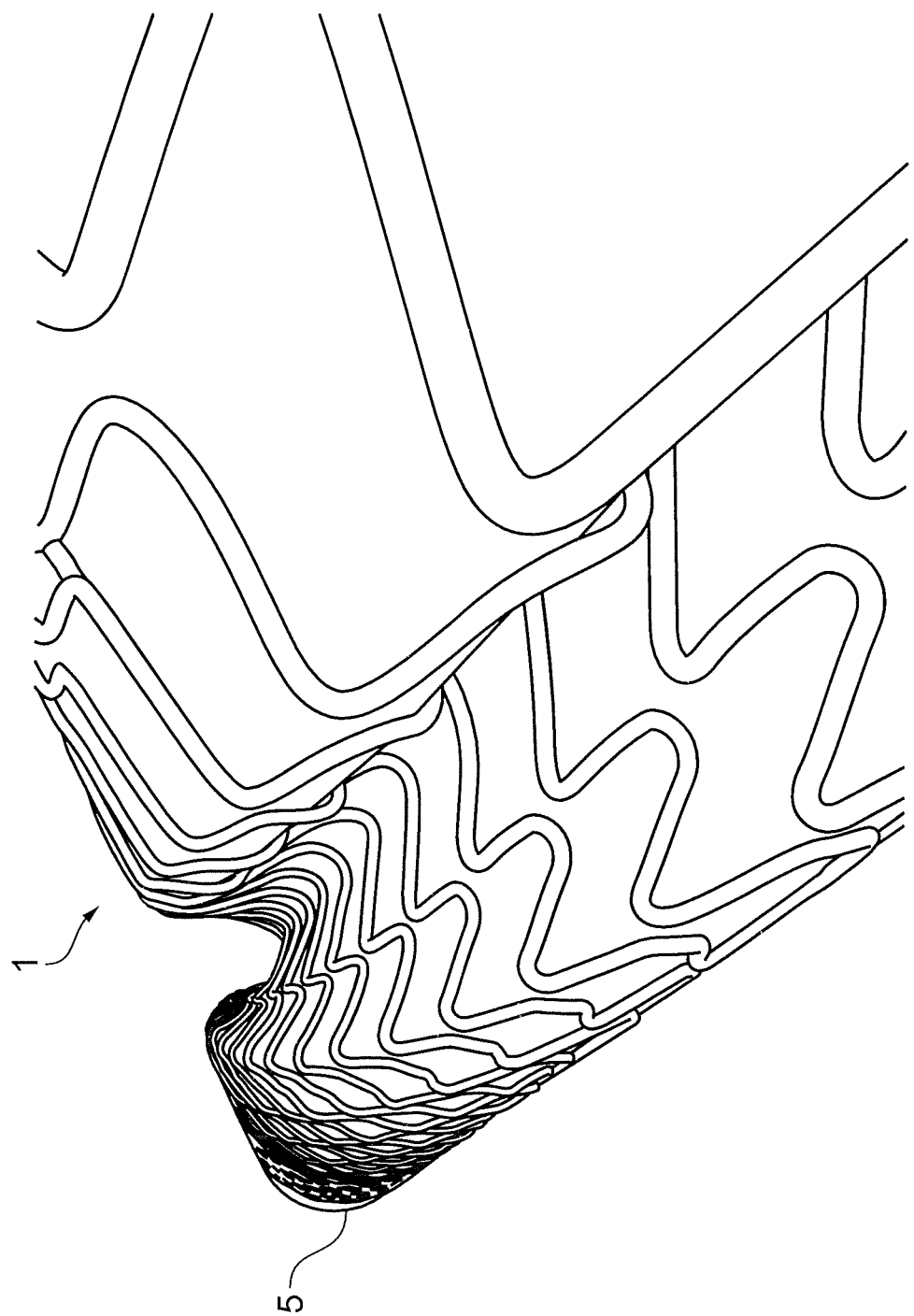
FIG. 9 is a perspective view of the stent of FIG. 1.

FIG. 2 illustrates a V-shaped bend 8 from a wave form and from within the helical fin 11 of the frame 2 of FIG. 1. A trough 7 is connected to two peaks 6 by two connecting struts (9a, 9b). The first connecting strut (9a) extends to the peak towards the centre of the helical fin 11. The angle of this strut is substantially aligned with the helix angle 14 of the helical fin 11. The second connecting strut (9b) extends to the peak away from the centre of the helical fin 11. The angle of this connecting strut 9b is the mirror angle of the angle of the first connecting strut 9a.

In the above-described embodiment, the tubular frame 2 comprises a network of struts in the form of a series of undulating rings 13. It is to be appreciated that each element in a ring comprising four peaks 6, four troughs 7 and one linker-strut may be considered to be a repeating element of the frame 2 and thus the struts that form the tubular frame 2 may be considered to be arranged as a series of repeating elements. In this regard, it will also be appreciated that the repeating elements are not strictly identical across the whole of the tubular frame 2 since the struts at the helical fin 11 are deformed in order to form the side walls of the helical fin 11. Nevertheless, it is possible to recognise that the repeating elements are present even in the struts of the helical fin 11, subject to some deformation thereof. It is to be understood that each repeating element within the tubular frame 2 comprises a certain strut length, that is to say the total length of each strut, and that in the tubular frame 2 outside of the helical fin 11, the fraction of the total strut length in each repeating element which is aligned with the helical fin 11 is relatively low (less than 10% of the total). On the other hand, within the helical fin 11, the fraction of the total strut length which is aligned with the helical fin 11 is almost 50%.

In variants of this embodiment, the fraction of the total strut length aligned with the helical fin 11 of the repeating elements in the helical fin 11 can approach 50%. However, in other embodiments, the fraction of the total strut length aligned with the helical fin 11 in each repeating element in the helical fin 11 is lower and may, for example, be 10%, 20%, 30% or 40%. However, in these embodiments the fraction of the total strut length of the repeating elements in the helical fin 11 which is aligned with the helical fin is greater than in the repeating elements outside of the helical fin 11. For example, the repeating elements outside of the helical fin may have a fraction of the total strut length aligned with the helical fin of less than 5% whereas within the helical fin the fraction of the total strut length in each repeating element which is aligned with the helical fin may be at least 10%, at least 20%, at least 30%, at least 40% or 50%. In this regard, it is to be appreciated that in some embodiments, the repeating element is not a part of an undulating ring and may, instead, be a cell such as a diamond shape cell within the frame as will now be described.

While the above-described embodiments of the stent 1 have a helical fin 11 which is not limited to any particular helix angle, a helix angle of between 5° and 50° with the longitudinal axis of the stent frame is typical. For example, the helical fin may have a helix angle of between 5° and 25°, preferably between 18° to 22°. It is preferred that the helix angle of the helical fin 11 is selected such that the helical fin 11 completes one whole turn around the longitudinal axis of the stent 1, within the length of the stent 1. In embodiments where the stent 1 is relatively short, it is desirable for the helix angle of the helical fin 11 to be relatively high in order to impart helical flow on the fluid passing therethrough, when implanted. As such, in some embodiments, the helix angle is typically between 20° and 40°.

Figure 10:
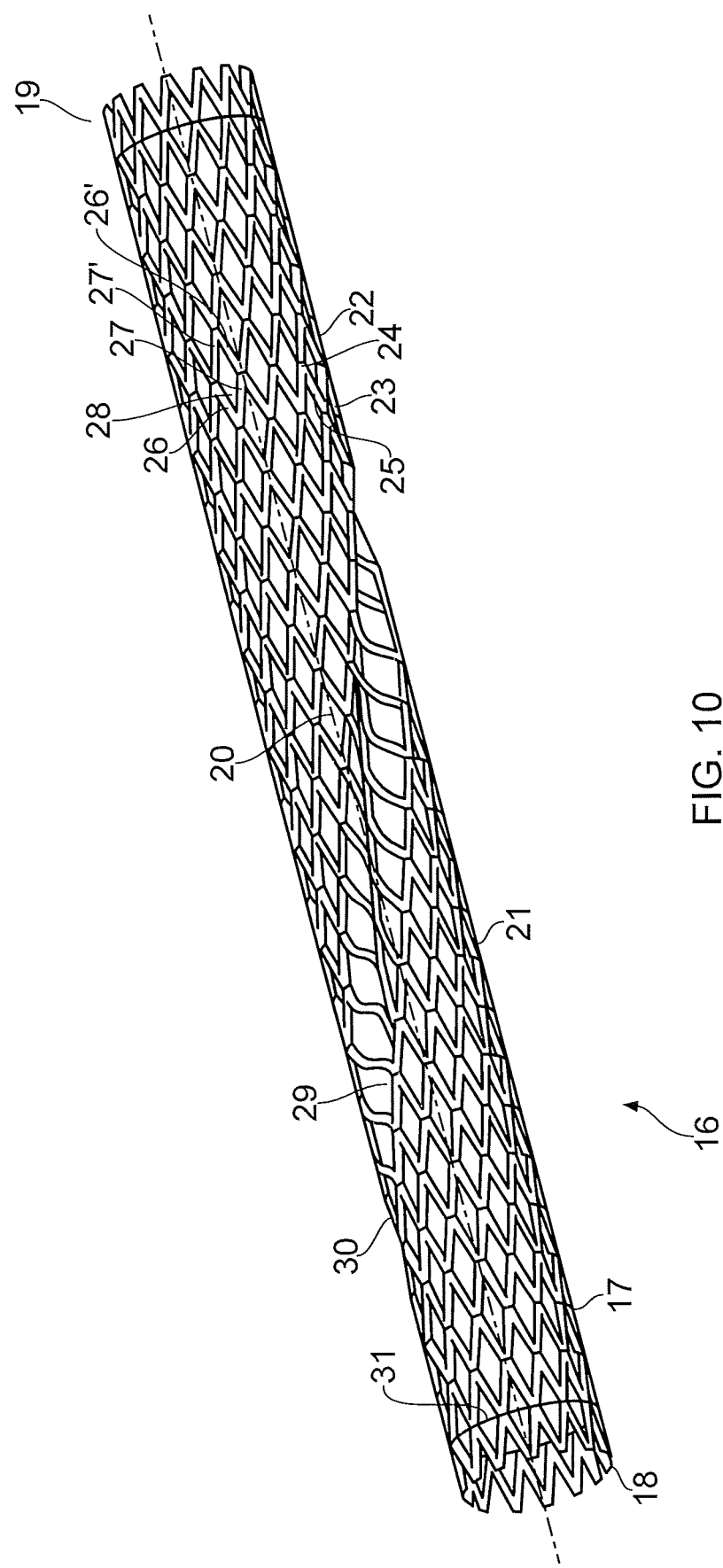
FIG. 10 is a perspective view of a stent in accordance with another embodiment of the present invention.
Figure 11:
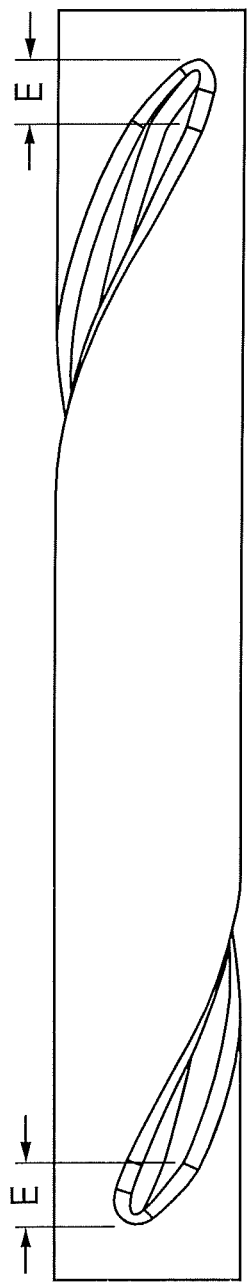
FIG. 11 is a schematic side view of a stent in accordance with another embodiment of the present invention with some details omitted.
Figure 12:
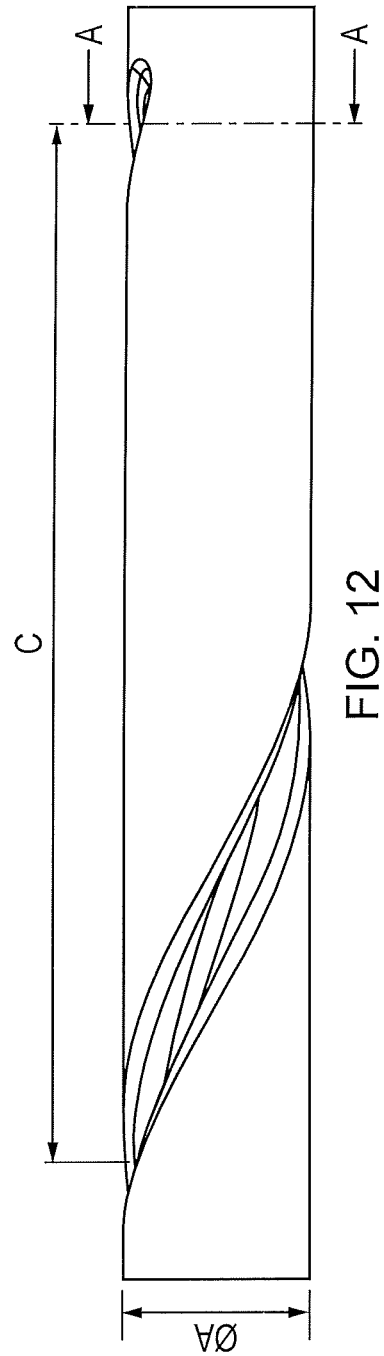
FIG. 12 is a schematic side view of a stent in accordance with the embodiment of FIG. 11 from a different rotational angle with some details omitted.
Figure 13:
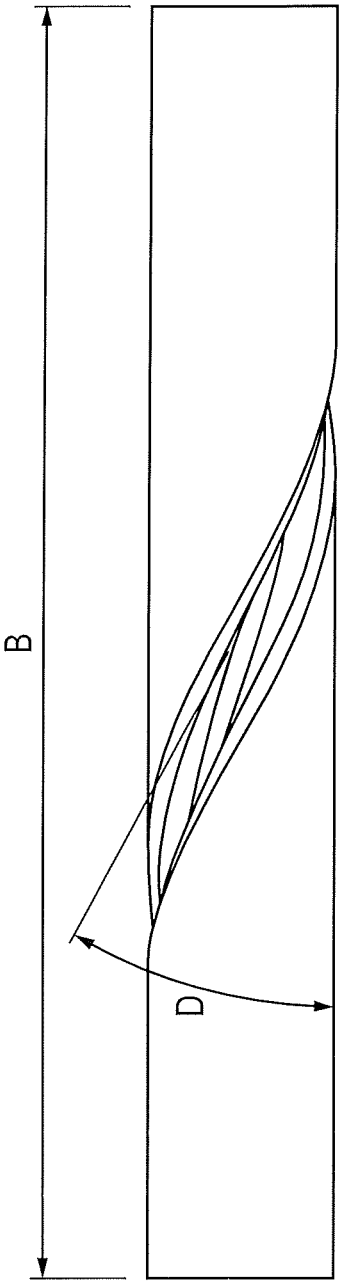
FIG. 13 is a schematic side view of a stent in accordance with the embodiment of FIG. 11 from a different rotational angle with some details omitted.
Figure 14:
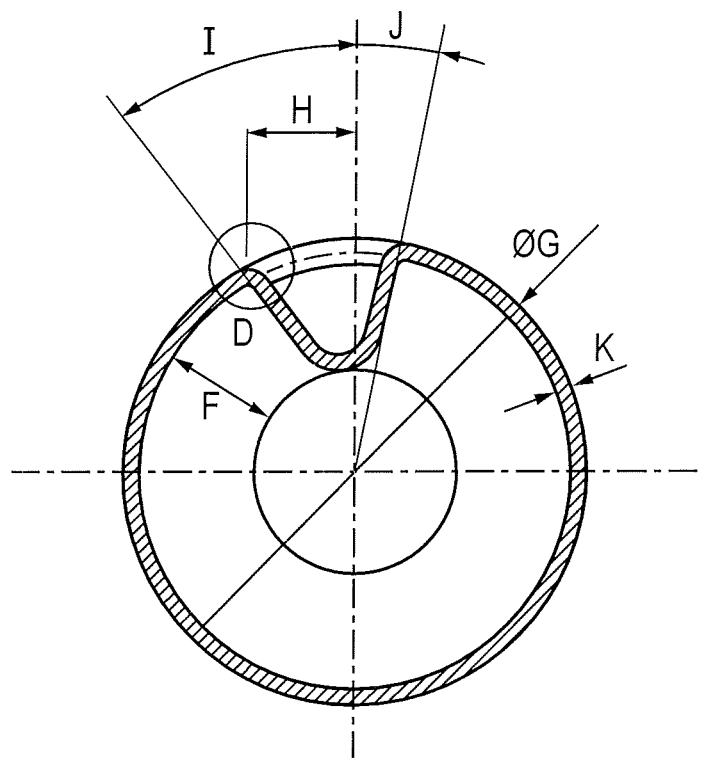
FIG. 14 is a schematic view along the line A-A of FIG. 12.
Figure 15:
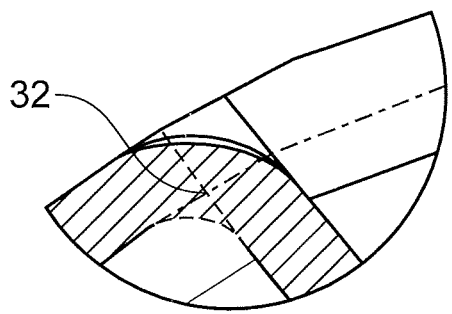
FIG. 15 is a close-up view of the circled area in FIG. 14.

Referring to FIG. 10, a second embodiment of the present invention is shown. A stent 16 has a tubular frame 17 having a first end (distal) 18 and a second end (proximal) 19 and a longitudinal axis 20 therebetween. The tubular frame 17 comprises a network of struts 21 in the form of a series of rings 22 which each have a triangle wave form. The series of rings 22 is disposed circumferentially along the longitudinal axis 20 of the tubular frame 17 and the rings 22 are arranged parallel to each other. Each ring 22 comprises a plurality of peaks 23 extending towards the first end 18 of the tubular frame 17 and a plurality of troughs 24 extending towards the second end 19 of the tubular frame 17. Each peak 23 and trough 24 forms a V-shaped bend 25 in the same plane as the cylindrical surface defined by the tubular frame 17. Each trough 24 of each ring 23 abuts, and is connected to, a peak 23 in the adjacent ring 22 which is further towards the second end 19 of the tubular frame 17. The exception to this is the ring 22 at the second end 19 which only has an adjacent ring on its side closest to the first end 18.

Each V-shaped bend 25 comprises a leading strut 26, which is angled to the left when viewed from the first end 18 to the second end 19 of the tubular frame 17, and a trailing strut 27, which is angled to the right when viewed from the first end 18 to the second end 19 of the tubular frame 17. Each leading strut 26 and its respective trailing strut 27 meet at the peak 23 of their V-shaped bend 25. It is to be appreciated that, owing to the alignment of adjacent rings 22, the leading strut 26 and the trailing strut 27 of each V-shaped bend 25 in a first ring 22 are aligned with the trailing strut 26' and the trailing strut 27' of a second and adjacent ring 22 to form a diamond-shaped cell 28.

A portion of the side wall of the tubular frame 17 is deformed radially inwardly to form a longitudinally extending helical fin 29. The helical fin defines an inducer path 30. The angle of each trailing strut 27 within the helical fin 29, relative to the longitudinal axis 20 of the tubular frame 17 is aligned with the helix angle of the helical fin 29, itself. The angle of each leading strut 26 within the helical fin, relative to the longitudinal axis 20 of the tubular frame 17, is deformed in order to form the helical fin.

Thus, in this embodiment, each V-shaped bend 25 can be considered to be a repeating element within the tubular frame 17. Within the helical fin, 50% of the strut length of each repeating element is aligned with the helix angle of the helical fin 29 since all trailing struts 27 are aligned with the helix angle of the helical fin 29 and the trailing struts 27 comprise 50% of each ring 22, with the remaining strut length comprising the leading struts 26.

Located within the lumen defined by the tubular frame 17, is a cover 31 made from PTFE, which is positioned to lie flat against the inner surface of the lumen. The cover therefore separates the contents of the lumen from the tubular frame 17.

The manufacture of embodiments the invention will now be described. In preferred embodiments of the present invention, the tubular frame 2, 17 is made from nitinol. Nitinol can be formed into a "memory" shape by constraining the material onto a mandrel or similar fixture and then performing a heat treatment. The treatment should be such that the temperature is reached through the entire cross section of the material. Once formed, the nitinol can be cooled and reshaped into its original shape. Once deformed, it will remain so until heated to its transformation temperature, the nitinol then expands to its stronger "memory" shape.

An exemplary method of forming a stent of the present invention comprises preparing a stent blank (ie. a stent without a helical fin) of a preferred frame geometry, preferably by laser cutting said pattern in a nitinol tube. The frame is cut such that the angle of the struts that will form the helical formation is aligned with the desired helical angle. This step provides a stent blank having a frame comprising a first end and a second end and a longitudinal axis therebetween, wherein the frame comprises a plurality of struts. The stent blank comprises a helical element extending longitudinally along at least a portion of the length of the frame and having a helix angle. The angle of at least some of the struts along the helical element is substantially aligned with the angle of the helical element.

It will be appreciated that the method of the invention can be used to introduce a helical fin into a stent of any frame geometry. In this exemplary method the frame is laser cut to provide a diameter of 2 mm. The frame is then supported on a mandrel of a 4 mm diameter. The frame is then heated at a temperature of between 400° C. and 600° C. for a time effective for the material to be exposed to the temperature. The laser frame is then expanded on a mandrel with a diameter of 6 mm and heat set at a temperature of between 400° C. and 600° C. for a time effective for the material to be exposed to the temperature. The expanded stent blank (i.e. a stent without a helical fin) is then further expanded by placing the frame onto a 8 mm customised mandrel having a female helical groove. The frame is then effectively clamped between the mandrel and a corresponding clamshell tool having a corresponding male ridge. This step creates the helical fin. The frame is then set at a temperature of between 400° C. and 600° C. to set the helical fin for a time effective for the material to be exposed to the temperature.

The material is then removed from the mandrel and the finished frame can be used as the frame for a completed stent.

It will be appreciated that any desired mandrel diameter can be used at each step of the process. The diameter used depends on the desired diameter of the finished stent. Typically, the first diameter is a quarter of the desired final diameter.

The correct helix angle of the helical fin is the angle that provides the desired non-turbulent flow in the fluid that flows through the frame.

In order to be used, the stent of the present invention is implanted into a patient, usually by a surgeon, by a method known in the art. In the process, the stent is crimped and inserted into the lumen of the blood vessel of the patient. Once positioned correctly, the stent is then expanded, either by balloon expansion or due to its self-expanding properties, thus compressing against the inner walls of the lumen. If expanded by a balloon catheter, the catheter is then removed by the surgeon. The stent substantially retains this expanded configuration. In vivo, the stent is under compression by the blood vessel. By virtue of the alignment of the connecting struts in the helical fin, the stent of the present invention resists radial compression and avoids fractures.

In embodiments in which the stent is inserted into a narrowed or blocked blood vessel, the outer wall of the stent compacts any plaques present thereby reopening the vessel lumen and allowing normal blood flow to resume.

It will be appreciated that in certain embodiments the stent is inserted as a precautionary measure, prior to any blockage or to provide support to weakened vessels.

When in use, the radially inwardly extending helical fin 11, 29 generates desirable flow characteristics in blood flowing through the lumen of the stent, by imparting spiral flow on the blood.

The helical fin 11, 29 extends radially inwardly for a distance equal to between 40% and 70% of the distance from the longitudinal axis of the frame to an internal side wall. Preferably, for a distance equal to between 40% and 60%, more preferably, for a distance equal to between 45% and 55%. Most preferably, the inwardly extending portion extends inwardly for a distance equal to substantially 50% of the distance from the longitudinal axis of the conduit to an internal side wall. Where the stent has a circular cross-section, the distance is as a percentage of the stent of the conduit.

The helical fin 11, 29 may have a constant helix angle along at least a part of its length, or one which reduces or increases over at least part of its length. The fin may taper in the direction of the blood flow or in the opposite direction.

The helical fin 11, 29 may have a V-shaped cross section, a square shaped cross section, a U-shaped cross section or a bell-shaped cross section. The fin may have a symmetrical cross section or an asymmetrical cross section.

The stent of the present invention may also comprise a cover or sheath. The effect of the cover is to cushion the blood vessel or, if provided on the inner surface of the stent, the cover protects the bloodstream from the stent frame.

While the above-described embodiments have related to vascular stents, it is to be understood that the present invention is not limited to any particular kind of vascular stent. Thus, in embodiments of the invention, the stent is a coronary stent, a peripheral arterial stent, a venous stent, a biliary stent, a ureteral stent or the like.

Example—Exemplification of Stent Structures

A stent design, in accordance with embodiments of the present invention, is provided as is shown in accordance with FIGS. 11 to 15. (In FIGS. 11 to 15, the stent frame, and other details, are omitted with only the helical fin shown). The stent design comprises a helical fin having an asymmetric cross-section. Table 1 shows possible configurations for the dimensions of the stent design. The labels A to K in FIGS. 11 to 15 represent the following dimensions of the stent design.

A represents the outer diameter of the stent in mm.
B represents the overall length of the stent in mm.
C represents the length of the main section of the helical fin along the longitudinal axis of the stent in mm.
D represents the helix angle of the helical fin in degrees.
E represents the length of the runout of the helical fin; that is the linear distance in mm along the longitudinal axis of the stent within which the helical fin terminates by the depth of the helical fin tapering to zero.
F represents the height in mm of the helical fin measured internally.
G represents the internal diameter of the stent in mm measured from one inside face to the perpendicular opposite inside face.
H represents the distance in mm between the point 32 and the diameter which intersects the curved surface of the helical fin. A more detailed explanation of this measurement can be found in WO2005/004751 on page 6.
I represents the angle between the following surface of the helical fin (i.e. the surface which is downstream in the fluid flow when the stent is implanted) and the vertical diameter described in reference to H above.
J represents the angle between the leading surface of the helical fin (i.e. the surface which is upstream in the fluid flow when the stent is implanted) and the vertical diameter described in reference to H above.
K represents the maximal thickness in mm of the tubular frame of the stent design.

TABLE 1

Table showing exemplary values for the dimensions shown in the stent design of FIGS. 11 to 15

| Stent Size | Dimensions | | | | | | | | | | |
| --- | --- | --- | --- | --- | --- | --- | --- | --- | --- | --- | --- |
| | A | B | C | D | E | F | G | H | I | J | K |
| 5 mm × 40 mm (V10) | 5 | 40 | 32.21 | 26 | 2.5 | 1.25 | 4.6 | 1.15 | 38 | 10 | 0.197 |
| 5 mm × 60 mm (V11) | 5 | 60 | 51.38 | 17 | 2.5 | 1.25 | 4.6 | 1.15 | 38 | 10 | 0.197 |
| 6 mm × 40 mm (V1) | 6 | 40 | 32.65 | 30 | 2.5 | 1.5 | 5.6 | 1.4 | 38 | 10 | 0.197 |
| 6 mm × 60 mm (V4) | 6 | 60 | 51.79 | 20 | 2.5 | 1.5 | 5.6 | 1.4 | 38 | 10 | 0.197 |
| 6 mm × 80 mm (V14) | 6 | 80 | 70.35 | 15 | 2.5 | 1.5 | 5.6 | 1.4 | 38 | 10 | 0.197 |
| 6 mm × 100 mm (V15) | 6 | 100 | 88.68 | 12 | 2.5 | 1.5 | 5.6 | 1.4 | 38 | 10 | 0.197 |
| 6 mm × 120 mm (V16) | 6 | 120 | 106.9 | 10 | 2.5 | 1.5 | 5.6 | 1.4 | 38 | 10 | 0.197 |
| 7 mm × 40 mm (V2) | 7 | 40 | 32.6 | 34 | 2.5 | 1.75 | 6.6 | 1.65 | 38 | 10 | 0.197 |
| 7 mm × 60 mm (V5) | 7 | 60 | 51.81 | 29 | 2.5 | 1.75 | 6.6 | 1.65 | 38 | 10 | 0.197 |
| 7 mm × 80 mm (V17) | 7 | 80 | 71.93 | 17 | 2.5 | 1.75 | 6.6 | 1.65 | 38 | 10 | 0.197 |
| 7 mm × 100 mm (V18) | 7 | 100 | 88.2 | 14 | 2.5 | 1.75 | 6.6 | 1.65 | 38 | 10 | 0.197 |
| 7 mm × 120 mm (V19) | 7 | 120 | 113.13 | 11 | 2.5 | 1.75 | 6.6 | 1.65 | 38 | 10 | 0.197 |
| 8 mm × 40 mm (V3) | 8 | 40 | 32.17 | 38 | 2.5 | 2 | 7.6 | 1.9 | 38 | 10 | 0.197 |
| 8 mm × 60 mm (V6) | 8 | 60 | 51.53 | 26 | 2.5 | 2 | 7.6 | 1.9 | 38 | 10 | 0.197 |
| 8 mm × 80 mm (V20) | 8 | 80 | 72.99 | 19 | 2.5 | 2 | 7.6 | 1.9 | 38 | 10 | 0.197 |
| 8 mm × 100 mm (V21) | 8 | 100 | 87.65 | 16 | 2.5 | 2 | 7.6 | 1.9 | 38 | 10 | 0.197 |
| 8 mm × 120 mm (V22) | 8 | 120 | 108.86 | 13 | 2.5 | 2 | 7.6 | 1.9 | 38 | 10 | 0.197 |

The invention claimed is:

1. A stent having a crimped configuration of a first diameter to allow insertion into a vessel of a patient and an expanded configuration of a second diameter, said stent comprising a tubular frame comprising a first end and a second end and a longitudinal axis therebetween, wherein the frame comprises a plurality of struts defining a generally cylindrical portion having an internal radius, and wherein said frame comprises a longitudinally extending helical fin having a centre, said fin protruding radially inwardly for a distance equal to between 40% and 70% of the internal radius of the cylindrical portion, and said fin having a helix angle, and wherein the struts delineate a plurality of circumferential rings having a wave form, wherein the wave form comprises a plurality of peaks extending towards the first end of the frame and a plurality of troughs extending towards the second end of the frame, wherein: i) a trough-to-peak connecting strut connects each trough to a peak, and ii) within the helical fin each trough-to-peak connecting strut connecting to a peak located towards the centre of the helical fin has an angle which is substantially the same as the helix angle of the helical fin.

2. The stent of claim 1, wherein each successive trough on adjacent rings within the helical fin is aligned with the helical fin.

3. The stent of claim 1, wherein the cross-sectional shape of the helical fin is asymmetric.

4. The stent of claim 1, wherein the helical fin is formed by the deformation of at least a portion of a side wall of the frame.

5. The stent of claim 1, wherein the helix angle is selected from the group consisting of: between 5° and 50°, between 18° and 22° and between 20° and 40°.

6. The stent of claim 1, wherein the wave form is selected from the group consisting of a triangle wave form, a sine wave form and a square wave form.

7. The stent of claim 1, wherein the rings comprise a number of cells.

8. The stent of claim 7, wherein the shape of the cells is selected from the group consisting of: a diamond shape, an open cell configuration, a closed cell configuration, and a combination thereof.

9. The stent of claim 1, wherein the frame is composed of a material selected from the group consisting of: self-expanding material, nickel titanium (nitinol), stainless steel, and cobalt-chromium alloy.

10. The stent of claim 1, comprising at least one cover.

11. The stent of claim 10, wherein the at least one cover comprises polytetrafluoroethylene (PTFE).

12. The stent of claim 10, wherein the location of the at least one cover is selected from the group consisting of:
   (i) over the inner surface of the frame,
   (ii) over the outer surface of the frame,
   (iii) over the helical fin only,
   (iv) and a combination of (i) and (ii).

13. The stent of claim 10, wherein the at least one cover is heat sealed to the frame.

* * * * *